US009797923B2

(12) United States Patent
Alvis

(10) Patent No.: US 9,797,923 B2
(45) Date of Patent: Oct. 24, 2017

(54) FABRICATION OF A MALLEABLE LAMELLA FOR CORRELATIVE ATOMIC-RESOLUTION TOMOGRAPHIC ANALYSES

(71) Applicant: FEI Company, Hillsboro, OR (US)

(72) Inventor: Roger Alvis, Beaverton, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/627,770

(22) Filed: Feb. 20, 2015

(65) Prior Publication Data

US 2015/0253353 A1 Sep. 10, 2015

Related U.S. Application Data

(60) Provisional application No. 61/948,516, filed on Mar. 5, 2014.

(51) Int. Cl.
*G01Q 30/02* (2010.01)
*G01N 1/00* (2006.01)
*G01Q 30/20* (2010.01)
*H01J 37/285* (2006.01)
(Continued)

(52) U.S. Cl.
CPC .............. *G01Q 30/02* (2013.01); *G01N 1/00* (2013.01); *G01N 1/32* (2013.01); *G01Q 30/20* (2013.01); *H01J 37/285* (2013.01); *G01N 2001/282* (2013.01); *H01J 2237/2802* (2013.01); *H01J 2237/2852* (2013.01);
(Continued)

(58) Field of Classification Search
CPC .................................................... G01Q 30/02
See application file for complete search history.

(56) References Cited

U.S. PATENT DOCUMENTS 7,442,924 B2 10/2008 Giannuzzi et al.
8,912,491 B2 12/2014 Schoenmakers et al.
(Continued)

FOREIGN PATENT DOCUMENTS

JP 2005233786 9/2005
JP 2010243458 10/2010
(Continued)

OTHER PUBLICATIONS

McKenzie et al., "Focused ion beam sample preparation for atom probe tomography", Microscopy: Science, Technology, Applications and Eductation. 2010.*
(Continued)

*Primary Examiner* — Michael Logie
(74) *Attorney, Agent, or Firm* — Scheinberg & Associates, P.C.; Michael O. Scheinberg

(57) ABSTRACT

A method of forming a sample and performing correlative S/TEM and APM analysis is provided wherein a sample containing a region of interest is cut from a bulk of sample material and formed into an ultra-thin lamella. The lamella is then analyzed with an S/TEM to form an image. The lamella sample and mount may then go through a cleaning process to remove any contamination. The lamella containing the ROI is then embedded within a selected material and is formed into a needle-shaped sample. The needle-shaped sample is then analyzed with the APM and the resulting data is merged and correlated with the S/TEM data.

17 Claims, 6 Drawing Sheets

(51) Int. Cl.
*G01N 1/32* (2006.01)
*G01N 1/28* (2006.01)

(52) U.S. Cl.
CPC .............. *H01J 2237/31745* (2013.01); *H01J 2237/31749* (2013.01); *Y10T 428/2933* (2015.01); *Y10T 428/2958* (2015.01)

(56) References Cited

U.S. PATENT DOCUMENTS

| | | | | |
|---|---|---|---|---|
| 2004/0056195 | A1* | 3/2004 | Kuhlman | G01N 1/06 250/307 |
| 2005/0029452 | A1* | 2/2005 | Furukawa | H01J 37/22 250/311 |
| 2005/0244668 | A1* | 11/2005 | Narita | C22C 14/00 428/610 |
| 2007/0158566 | A1* | 7/2007 | Ikeda | G01N 1/32 250/311 |
| 2008/0156770 | A1* | 7/2008 | Munekane | H01J 37/20 216/66 |
| 2010/0152052 | A1* | 6/2010 | Goodman | G01N 1/36 506/7 |
| 2011/0103681 | A1* | 5/2011 | Kelly | B82Y 15/00 382/154 |
| 2012/0080596 | A1* | 4/2012 | Vandervorst | H01J 37/226 250/307 |
| 2013/0214468 | A1* | 8/2013 | Giannuzzi | H01J 37/20 269/287 |
| 2013/0248354 | A1 | 9/2013 | Keady et al. | |
| 2013/0319849 | A1 | 12/2013 | Fuller et al. | |
| 2013/0328246 | A1 | 12/2013 | Wells et al. | |
| 2014/0070095 | A1 | 3/2014 | Schoenmakers et al. | |
| 2015/0048244 | A1* | 2/2015 | Akutsu | H01J 49/164 250/282 |
| 2015/0060695 | A1* | 3/2015 | Man | H01J 37/317 250/442.11 |

FOREIGN PATENT DOCUMENTS

WO 2007075908 A2 7/2007
WO 2012103534 8/2012

OTHER PUBLICATIONS

Gault et al., "Sample Preparation", Atom Probe microscopy, vol. 160 of the series Springer series in Material Science pp. 71-110. Apr. 2, 2012.*
Felfer et al. "New equipment for Correlative FIB/TEM/Atom Probe and Site-Specific Preparation Using STEM Live Imaging", microsc. Microanal. 17 (suppl 2), 2011.*
Kempshall et al., "Comparative evaluation of protective coatings and focused ion beam chemical vapor deposition processes", American Institute of Physics, 2002.*
Jin, S., et al., "Pulsed-laser atom probe tomography of p-type field effect transistors on Si-on-insulator substrates," Journal of Vacuum Science Technology B, 2011, pp. 061203-1 to 061203-4, vol. 29, No. 6.
Lee, J. H., et al., "3D Compositional Characterization of Si/SiO2 Vertical Interface Structure by Atom Probe Tomography," Electron. Mater. Lett., 2013, pp. 747-750, vol. 9, No. 9.
Lewis, et al., "Meteoritic Nanodiamond Analysis by Atom-Probe Tomography", 43rd Lunar and Planetary Science Conference, 2012.
Alvis, et al., "High-Throughput, Site-Specific Sample Prep of Ultra-Thin TEM Lamella for Process Metrology and Failure Analysis", 2012, FEI Company, Hillsboro, Oregon, USA.
Thompson, et al., "In Situ Site-Specific Specimen Preparation for Atom Probe Tomography", Ultramicroscopy, 2007, pp. 131-139, Issue No. 107.
Thompson, et al., "Imaging of Arsenic Cottrell Atmospheres Around Silicon Defects by Three-Dimensional Atom Probe Tomography", Science, 2007, p. 1370, Issue No. 317.
Ronsheim, et al., "Impurity Measurements in Silicon with D-SIMS and Atom Probe Tomography", Applied Surface Sience, 2008, pp. 1547-1550, Issue No. 255.
Koelling, et al., "Failure Mechanisms of Silicon-Based Atom-Probe Tips", Ultramicroscopy, 2008, pp. 486-491, Issue No. 109.
Inoue, et al., "Dopant Distributions in n-MOSFET Structure Observed by Atom Probe Tomography", Ultramictoscopy, 2009, pp. 1479-1484, Issue No. 109.
Mangelinck, et al., "Three-Dimensional Composition Mapping of NiSi phase distribution and Pt diffusion via Grain Boundaries in Ni2Si", Scripta Materalia, 2010, pp. 568-571, Issue No. 62.
Narayan, et al., "Chemical Mapping of Mammalian Cells by Atom ProbeTomography", Journal of Structural Biology, 2012, pp. 98-107, Issue No. 178.
Vurpillot, et al., "Reconstructing Atom Probe Data: A Review", Ultramicroscopy, 2013, pp. 19-30, Issue No. 132.
Du, et al., "Full Tip Imaging in Atom Probe Tomography", Ultramicroscopy, 2013, pp. 96-101, Issue No. 124.
Silaeva, et al., "Atom Probe Tomography and Field Evaporation of Insulators and Semiconductors: Theoretical Issues", Current Opinion in Solid State and Materials Science, 2013, pp. 211-216, Issue No. 17.
Larson, et al., "Atom Probe Tomography Spatial Reconstruction: Status and Directions", Current Opinion in Solid State and Materials Science, 2013, pp. 236-247, Issue No. 17.
Kambham, et al., "3D Site Specific Sample Preparation and Analysis of 3D Devices (FinFETs) by Atom Probe Tomography", Ultramicroscopy, 2013.
Henry Karen T., "Frontiers of Atom Probe Microscopy", Intel, 2013.
Ceguerra, et al., "The Rise of Computational Techniques in Atom Probe Microscopy", Current Opinion in Solid State and Materials Science, 2013, pp. 224-235, Issue No. 17.
Diercks, et al., "Atom Probe and (S)TEM Analysis of Semiconductor and Oxide Nanostructures", Intenational Conference of Frontiers of Characterization and Metrology for Nanoelectronics, 2013, Colorado School of Mines.
Alvis Roger, "Growing FEI's EBU SAM by Re-Purposing the S/TEM Lamella", FEI, 2013, IDF Submission Supplement.
Grenier, et al., "3D Analysis of Advanced Nano-Devices Using Electron and Atom Probe Tomography", Ultramicroscopy, 2014, pp. 185-192, Issue No. 136.
Unknown, http://fei.com/products/dualbeam/helios-nanolab; accessed Feb. 10, 2014.
Unknown, http://www.vsg3d.com/avizo/overview, accessed Feb. 10, 2014.

* cited by examiner

FABRICATION OF A MALLEABLE LAMELLA FOR CORRELATIVE ATOMIC-RESOLUTION TOMOGRAPHIC ANALYSES

This Application claims priority from U.S. Provisional App. 61/948,516, filed Mar. 5, 2014, which is hereby incorporated by reference.

TECHNICAL FIELD OF THE INVENTION

The present invention relates to a process of forming a sample that can be used for transmission electron microscopy and atom probe microscopy.

BACKGROUND OF THE INVENTION

Tomography is a rapidly advancing imaging technology with broad applications in such varied fields such as, for example, medicine, dentistry, biology, environmental, toxicology, mineralogy, and electronics. Tomography is the process of forming a 3-D image of a sample using various tools, such as, an x-ray system, a transmission electron microscope (TEM), scanning transmission electron microscope (STEM), and/or atom probe microscopy (APM) to obtain various types of information such as, for example, atomic structure and chemical analysis of the sample. A 3-D tomography dataset is typically obtained from a photon (e.g., optical or x-ray) or electron microscope by reconstructing a series of 2-D projection images taken through the sample at different angles, or in the case of an APM by reconstructing a volume from a sequence of field-evaporated atoms striking a position-sensitive detector.

TEMs and STEMS allow observers to see extremely small features, on the order of nanometers, and allow analysis of the internal structure of a sample. For convenience, the reference to TEMs and STEMs will be indicated by the term "S/TEM" and references to preparing a sample for an S/TEM are to be understood to include preparing a sample for viewing on a TEM or a STEM. The sample must be sufficiently thin to allow many of the electrons in the beam to travel though the sample and exit on the opposite side. Thin S/TEM samples are typically cut from a bulk sample material and are known as "lamellae". Lamellae are typically less than 100 nm thick, but for some applications a lamella must be considerably thinner. In S/TEM tomography, an electron beam is passed through the lamella at incremental degrees of rotation to form a series of tilted two-dimensional projections through a thin sample from which a three-dimensional rendering of the original structure can be constructed.

Atomic probe microscopes (APMs) typically include a sample mount, an electrode, and a detector. During analysis, a sample is carried by the specimen mount and a positive electrical charge is applied to the sample. The sample is typically in the form of a pillar having a narrowed needle-shaped tip. The detector is spaced from the sample and is either grounded or negatively charged. The electrode is located between the sample and the detector, and is either grounded or negatively charged. An electrical pulse and/or laser pulse is intermittently applied to the sample to cause atoms at the tip of the needle to ionize and separate or "evaporate" from the sample. The ionized atoms, molecules, or clusters-of-atoms pass through an aperture in the electrode and impact the surface of the detector resulting in a detected ion or a "count." The elemental identity of an ionized atom can be determined by measuring its time of flight between the needle surface and the detector, which varies based on the mass/charge ratio of the ionized atom. The location of the ionized atom on the surface of the needle can be determined by measuring the location of the atom's impact on the detector. Accordingly, as the sample is evaporated, a three-dimensional map of the sample's constituents can be constructed.

S/TEM provides better structural data while APM provides better compositional data. The different tomographic data from either S/TEM or APM used alone prevents optimal material analysis. Correlative S/TEM and APM tomography utilizes data from both S/TEM and APM to obtain valuable structural and chemical information from the sample. The quality of data can vary depending on various aspects of the sample, such as, for example, size, shape, and density, and the composition and spatial distribution of features in the volume being analyzed. Current correlative S/TEM and APM tomography typically uses pillar-shaped needle samples that are nominally cylindrical and containing a region of interest (ROI). The quality of each individual S/TEM image in a tomographic series from a pillar sample is somewhat lower than can be achieved with a lamella sample as a result of, for example sample thickness and feature-obscuring projection effects. The quality of data from APM tomography data acquisition experiment depends largely on the three-dimensional arrangement of elements across the different areas of the sample. In general, an APM sample is elementally non-homogeneous, practically resulting in a sample having an indiscriminate number of and distribution of evaporation fields across the field-evaporating portion of the sample, each region of which must form a nominally hemispherical shape to simultaneously satisfy the basic equation governing field evaporation: $E_i = kV/r_i$, where $E_i$ is the evaporation field of the ith element of the surface of the APM sample, $r_i$ is the radius of the ith element of the surface of the APM sample, V is the voltage applied to the sample at any particular time in the data acquisition experiment, and k is a constant of proportionality that largely depends on the geometry of the electrode and sample. In the case where any one or more of the field-evaporating elements on the surface of the APM sample is unable to satisfy the requirements of the field-evaporation equation, the sample may spontaneously evaporate in an uncontrollable fashion (uncorrelated with voltage or laser pulse), leading to artifacts in the data or a catastrophic fracture of the sample. Additionally, it can be difficult to form a pillar sample with invisible or buried features of the ROI properly positioned within the pillar. Yet another drawback to correlating S/TEM and APM using a pillar sample is that with the field-of-view of an APM dataset is limited to approximately the inner 50% of the formed pillar shaped sample, a compromise exists between S/TEM data quality and analysis volume in the APM. Additionally, for those APM runs that make it through the ROI successfully, there are often significant distortions and artifacts in the raw data that cannot be adequately corrected for during the reconstruction or data rendering phase of the analysis. Current issues in APM data acquisition, reconstruction and analysis are described, for example, in Larson et al., "Atom probe tomography spatial reconstruction: Status and directions" *Current Opinion in Solid State and Materials Science* 17 (2013 pp. 236-247). Another problem with correlative S/TEM and APM tomography is that advanced S/TEM imaging and analytical techniques, such as, for example, holography, differential phase contrast, phase-plate contrast enhancement and even lattice imaging and analysis, are largely incompatible with a pillar-shaped sample.

SUMMARY OF THE INVENTION

An object of the invention, therefore, is to provide an analytical system that improves correlative S/TEM and APM analysis.

In some embodiments, a sample for correlative S/TEM and APM tomography provides quality data with the microstructural precision and resolution of S/TEM and the chemical sensitivity of the APM.

In some embodiments, a specimen is prepared that enables site-specific S/TEM and APM analysis that can consistently produce both high resolution S/TEM tilt-series data and minimally distorted APM data in a wide range of industrially relevant materials. The sample is preferably positioned onto an S/TEM- and APM-compatible sample holder so that an ultra-thin lamella containing a region of interest (ROI) can be milled and used for S/TEM analysis and then re-shaped into a needle-shaped sample for APM analysis. This provides a new sample form of an ROI that is located in the lamella embedded within the needle-shaped sample for the APM.

Some embodiments also provide methods of forming a needle-shaped sample for the APM side of correlative S/TEM and APM tomography. A thin lamella containing an ROI is formed from a bulk material and coated with a material selected to compliment the field evaporation property of the elemental components of the ROI. After the coating step is complete the lamella is formed into a needle-shaped sample for analysis with the APM.

Some embodiments further provide a method of performing correlative S/TEM and APM analysis. A sample containing an ROI is cut from a bulk of sample material and formed into a thin lamella. The lamella is then analyzed with an S/TEM to form an image. The lamella sample and mount may optionally be cleaned to remove any contamination that accumulates between the time of S/TEM imaging and subsequent re-processing of the sample for APM analysis. The lamella containing the ROI is then embedded within a selected material and is formed into a needle-shaped sample. The needle-shaped sample is then analyzed with the APM and the resulting data is merged and correlated with the S/TEM data.

While a lamella can be used for S/TEM analysis, a sample prepared in accordance with an embodiment of the invention provides improved APM data, and could be analyzed on the APM without also being observed on the S/TEM.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

In accordance with some embodiments, a lamella suitable for S/TEM analysis is prepared using a focused ion beam or other method. After optional observation on S/TEM, material is deposited onto the thin lamella to form a thicker structure with the lamella embedded. The thicker structure is then milled to form a needle-like structure for atom probe microscopy. Thus, following this general sequence, a region of interest extracted from a bulk sample can be optimized for S/TEM and then separately optimized for the APM analysis. The embedded lamella sample structure also shows improved field evaporation characteristics compared to the traditional cone- or needle shaped structure having the region of interest and surrounding original matrix material largely intact relative to their positions in the bulk substrate. The improved data from the two sources can be more easily correlated thus improving the accuracy of the three-dimensional reconstructed microstructure and composition of the sample. By correlating the data from the S/TEM and the APM, one gets the precise structural information from the S/TEM and the precise elemental information from the APM.

Figure 1:
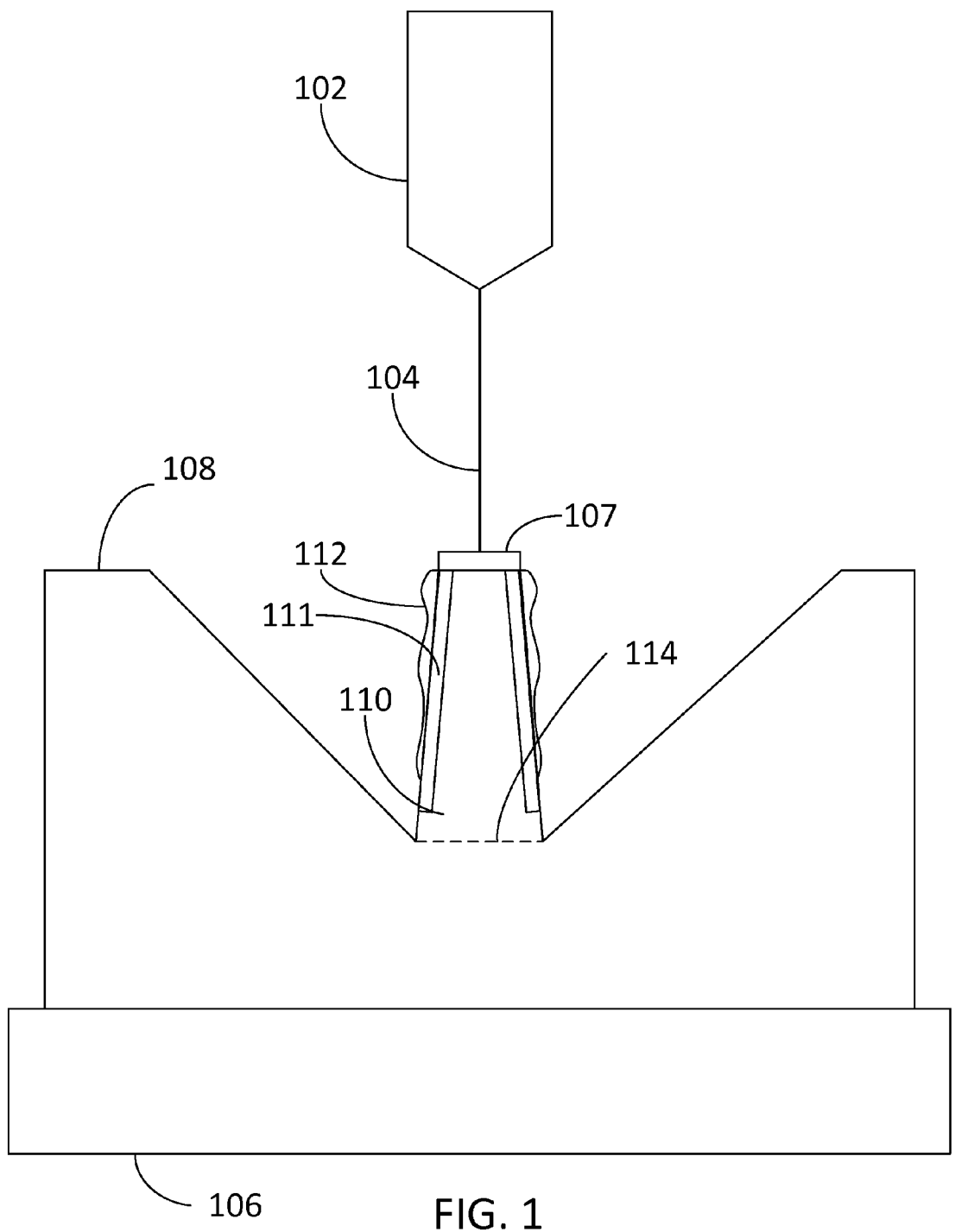
FIG. 1 shows a FIB system in an initial orientation for preparing a sample lamella for TEM analysis from a substrate.

According to some embodiments, a sample containing a region of interest (ROI) is cut from a bulk of material using standard FIB techniques. One example of cutting a sample from a bulk material is shown in FIG. 1. The bulk sample material 108 is loaded into sample stage 106 of the tool. The stage 106 may provide a plurality of motion axes, including translation, rotation, and tilting such that an optimal orientation of the sample may be achieved at each step of the lamella formation process. An FIB column 102 is shown in an orientation for performing initial milling on a bulk sample material to create a sample lamella for S/TEM analysis. In this embodiment, substrate 108 is oriented so that its top surface is perpendicular to focused ion beam 104 emitted from FIB column 102. Typically, a protective or capping layer 107 is deposited over the region of interest, for example, by beam-induced deposition of platinum, tungsten, or silicon dioxide, to protect the region of interest and to reduce ion milling artifacts. Alternatively or in addition to the beam-induced deposition previously described, a protective capping layer could be deposited on the surface of the sample prior to loading the sample into the focused ion beam system. Most of the coarse ion beam machining done to create lamella 110 is performed with substrate 108 and FIB column 102 in this orientation. Due to the focusing (i.e., a convergent conical shape) and the path of ion beam 104, this perpendicular milling causes lamella 110 to be tapered from top to bottom. That is, lamella 110 is thinner at the top than it is at the bottom. In this embodiment, lamella 110 remains securely attached to substrate 108 at boundary 114. For the case where lamella 110 is formed in a substrate larger than a few tens of micrometers in width or length, the lamella 110 must be removed from substrate 108 and thinned to electron transparency before it can be used in the S/TEM. In addition, material removed from substrate 108 while milling with ion beam 104 in the vertical orientation may be re-deposited onto the face of lamella 110, forming an undesirable layer 112 of foreign material. Likewise, the use of a high-energy focused ion beam to form a lamella in the substrate results in a thin intermixed layer of elements 111 at the FIB milled-surface materials and the species used for ion milling, typically gallium, argon, or xenon. The presence of layers 111 and 112 reduces the quality of the S/TEM analysis and must be removed or polished away before lamella 110 can be used with the S/TEM.

The FIB system may be repositioned in a tilted orientation for post-processing a sample lamella using over-tilting, polishing, and/or undercutting. Over-tilting is the process of removing the taper from the sides of lamella 110 to make the faces of lamella 110 substantially parallel. Polishing is the process of removing layer(s) 111 and 112 from lamella 110 that accumulated on lamella 110 from the previous initial milling. Undercutting is the process of partially or fully detaching lamella 110 from substrate 108 at or near boundary 114. Either sample stage 106 or FIB column 102 is rotated an angle 116 about the long axis of lamella 110. That is, either sample stage 106 or FIB column 102 is rotated an angle 116 relative to a plane defined by the long axis of lamella 110 and the normal to the top surface of substrate 108. Put another way, sample stage 106 or FIB column 102 is rotated about an axis that is perpendicular to the sheet of FIG. 1 and located within the cross-section of lamella 110 shown in FIG. 1, preferably near the center of the cross-section of lamella 110.

Figure 2:
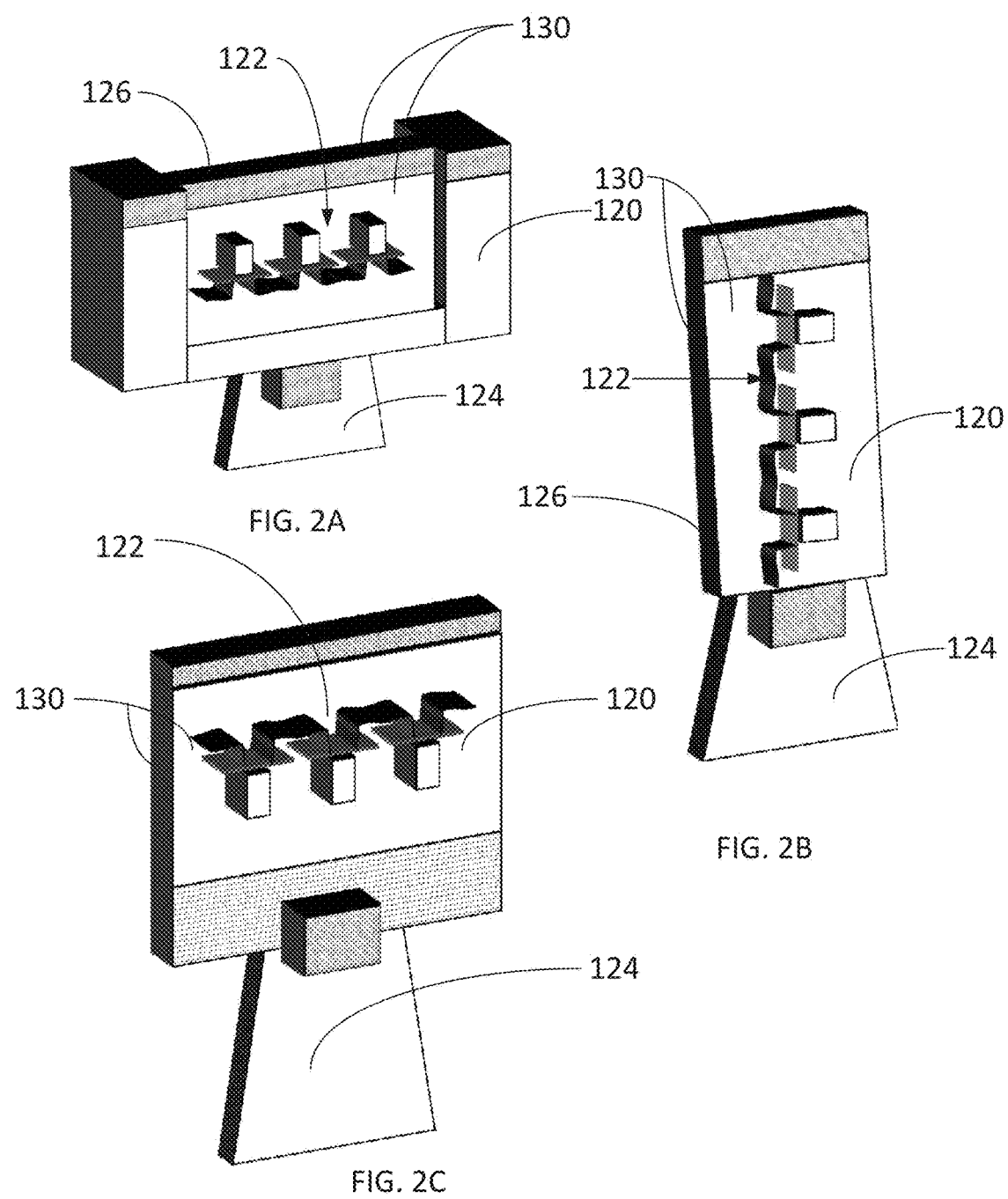
FIGS. 2A-2C show a sample lamella positioned on a mount in various orientations.

As seen in FIGS. 2A, 2B, and 2C, the lamella 120 containing the ROI 122 is then relocated to a mechanical mount 124 that is compatible with both S/TEM and APM systems. The lamella 120 is transferred using a motorized micromanipulator and attached to the mount using an ion or electron beam-induced deposition process, or using a mechanical mechanism, or adhesive material, in a known manner. The lamella 120 may be arbitrarily orientated on the mount 124. The orientation is chosen to provide the desired viewing in the S/TEM and in the APT. For example, as seen in FIG. 2A, the lamella 120 is shown with the ROI 122 positioned on the mount 124 in a "normal" orientation, that is, with the top surface 126 of the lamella in a substantially horizontal orientation. Alternatively, the lamella 120 may be placed on the mount 124 with the ROI 122 in a "90-degree flipped" orientation in which the original top surface 126 of the lamella 120 is rotated into a substantially vertical position as seen in FIG. 2B. Another option is seen in FIG. 2C, in which the lamella 120 is shown with the ROI 122 mounted in an "inverted" orientation relative to the orientation of the lamella as it was extracted from in the original bulk material. Each orientation can be employed advantageously to optimize the region of interest 122 for both sample preparation and APM analysis. The lamella 120 is then shaped on the mount through a series of FIB milling patterns to be as thin as possible. Ideally, the lamella 120 is shaped so that the sidewalls 130 are uniformly perpendicular and the lamella 120 is formed as thin as possible to ensure an unobstructed view of the ROI 122 during analysis using the S/TEM. The finished lamella 120 is very thin and may have a thickness of less than 100 nm. In some embodiments, the lamella 120 may have a thickness of less than 15 nm Preferably, the thickness of the viewing area of the lamella containing the ROI 122 varies by less than 25%, more preferably by less than 10%, and even more preferably by less than about 3% over the viewing area. The lamella 120 may be formed by any known conventional technique, including but not limited to mechanical shaping, and broad beam ion milling, in addition to the aforementioned focused ion beam milling methods. Examples include U.S. Pub. No. 2013/0319849 to Fuller et al for "Preparation of Lamellae for TEM Viewing," assigned to the assignee of the present invention, which is fully incorporated herein by reference, U.S. Pub. No. 2013/0248354 to Keady et al for "High Throughput TEM Preparation Processes and Hardware for Backside Thinning of Cross-Sectional View Lamella," assigned to the assignee of the present invention, which is fully incorporated herein by reference, and International Pub. No. WO 2012/103534 A1 to Blackwood et al for "TEM Sample Preparation," assigned to the assignee of the present invention, which is fully incorporated herein by reference. The lamella is then analyzed in the S/TEM in a known process.

After the lamella 120 has been analyzed with the S/TEM, the lamella 120 and mount 124 may be put through a cleaning process. The S/TEM study can include, for example, forming a single S/TEM image, EELS, EDS, electron holography, differential phase contrast, phase-plate contrast enhancement, and electron diffraction analyses. Heating, cooling, and even environmental exposure may be part of the S/TEM data acquisition methodology. Likewise, S/TEM tomography using any appropriate S/TEM technique, or combinations thereof may be used as part of the correlation with APM data. The cleaning process may be any known series of photon, plasma, gas, or liquid cleans to remove organic surface contamination, such as, for example, carbon, or etchants to selectively remove or reshape specific materials contained within the ROI.

Figure 3:
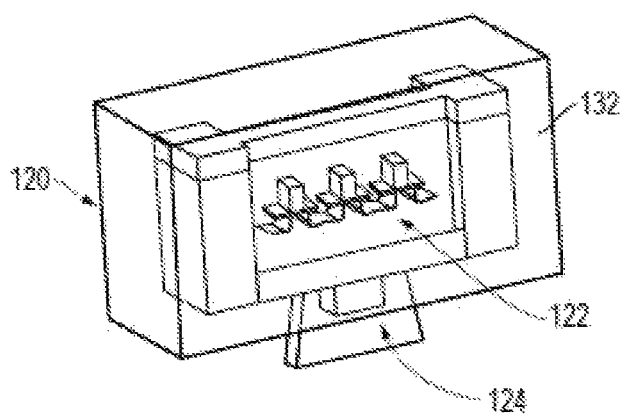
FIG. 3 shows a sample lamella with a material coating.

After the S/TEM study is completed, the lamella 120 and mount 124 is placed within a suitable deposition system, such as, for example, a SEM with an electron or ion beam induced deposition system, a FIB with an ultra-low kV column and a suitable ion source, PVD, or CVD. The lamella 120 is uniformly coated with a selected material 132 as seen in FIG. 3. The coating material 132 is preferably selected to compliment the field evaporation property of the elemental components within the ROI 122. For example, the coating material 132 may have a mass that is different from the mass of the ROI 122 making it easier to separate data of the coating material 132 from data of the lamella 120 in the APM. The coating material 132 is preferably relatively pure, fine grained and conformal such that gaps and voids may be filled and adherent such that an intimately bonded coating on the surface of the lamella is formed, as well as possible to deposit at relatively low temperatures. Examples of suitable coating materials include CVD and PVD silicon, and PVD nickel, cobalt, and chrome.

Figure 4:
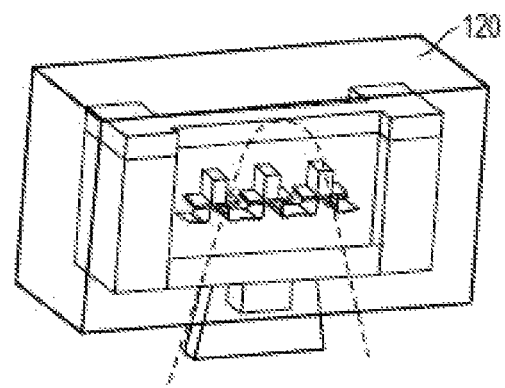
FIG. 4 is a view similar to FIG. 3 showing how the region of interest will be located within the tip of a needle-shaped sample.
Figure 5:
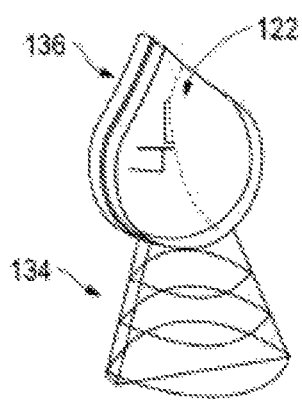
FIG. 5 is a stylized view of a needle-shaped sample with the region of interest located within the needle tip.

After the coating process the lamella is transferred back to the FIB where it is put through a series of sequential annular mills and shaped into a needle-shaped specimen in a known manner as seen in FIGS. 4 and 5. FIG. 4 shows the lamella 120 with a hypothetical needle tip shape shown in dashed lines for the understanding of the position of the ROI 122 within the tip of the needle-shaped sample. In most cases, it will be advantageous for the embedded part of the lamella to be nominally positioned along the diameter of the cone. FIG. 5 shows a stylized needle-shaped sample 134 with an exaggerated tip 136 for ease of understanding of location and position of the ROI 122 in the tip 136. However, it should be understood that the tip 136 is formed as more of a cone shape. Any preferred FIB mill process may be utilized to form the needle-shaped sample. One example is shown and disclosed in U.S. Pat. No. 7,442,924 to Giannuzzi et al for "Repetitive Circumferential Milling for Sample Preparation," assigned to the assignee of the present invention, which is fully incorporated herein by reference.

Figure 6:
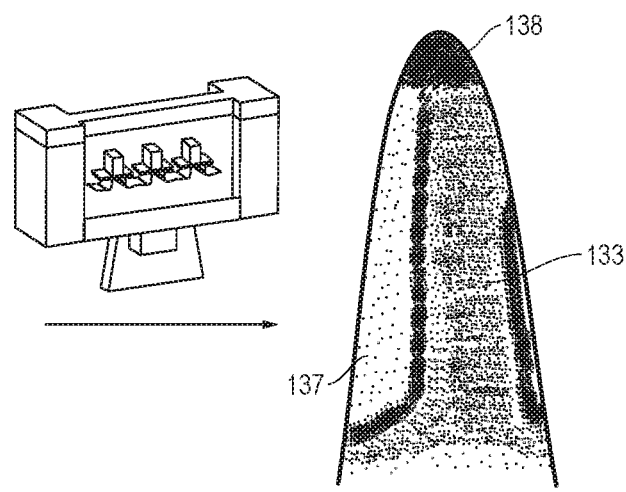
FIG. 6 shows a needle-shaped sample with the region of interest positioned for viewing in a direction perpendicular to the long axis of the cone.
Figure 7:
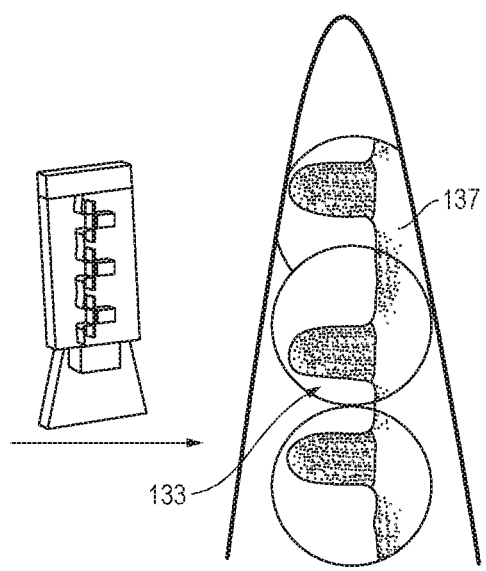
FIG. 7 is shows a needle-shaped sample with the region of interest positioned for viewing in a direction along the axis of the cone.

FIGS. 6 and 7 show a needle-shaped reconstructed APM data set 137 with the reconstructed ROI 133 in different orientations. FIG. 6 shows a needle-shaped or cone-shaped APM data set 137 formed with the reconstructed ROI 133 in the "normal" orientation as discussed above and shown in FIG. 2A. In this normal orientation the reconstructed ROI 133 starts well below the reconstructed capping layer 138 at the top of the data set and extends from the left of the data set to the right of the data set, nominally perpendicular to the long-axis of the conic shaped reconstructed data set 137. FIG. 7 shows a needle-shaped reconstructed data set 137 formed with the reconstructed ROI 133 in the "90-degree" orientation as discussed above and shown in FIG. 2B. In this orientation the reconstructed ROI 133 starts at the top of the data set and extends down into the bottom of the reconstructed data set 137, running parallel to the long-axis of the cone. In the real sample, the ROI 122 is buried in the bulk of the tip 136 preferably at a distance from the apex of the physical tip 136 between about 30 nm and 2 micrometers. Coating the ROI 122 with a selected material 132 provides a more uniform electric field over a larger extent of the needle tip 136 than would be achieved if the ROI were formed in a needle tip formed from the bulk sample material. The time- and position-variable electric field is then largely confined to the thin ribbon of inhomogeneous material in the embedded lamella. Because the width of the lamella is small compared to the diameter of the full tip, forming a complex tip shape as required by the governing equation describe previously is achieved by reshaping the material located on the exposed surface of the embedded lamella rather than across the entire surface of a more conventionally shaped tip formed by shaping a needle in the "bulk" of the sample. Therefore, an "embedded-lamella" APM specimen is more "malleable" than needle samples formed in a bulk specimen because the reduced area of complex tip shaping allows more controlled field evaporation and fewer field evaporation artifacts such as micro-fractures, and cluster and uncorrelated evaporation events.

After the FIB milling process is complete, the needle-shaped sample tip 136 is analyzed and reconstructed in the APM and the digitized microstructure is visualized and merged or correlated with the S/TEM data using separate software tools.

Figure 8:
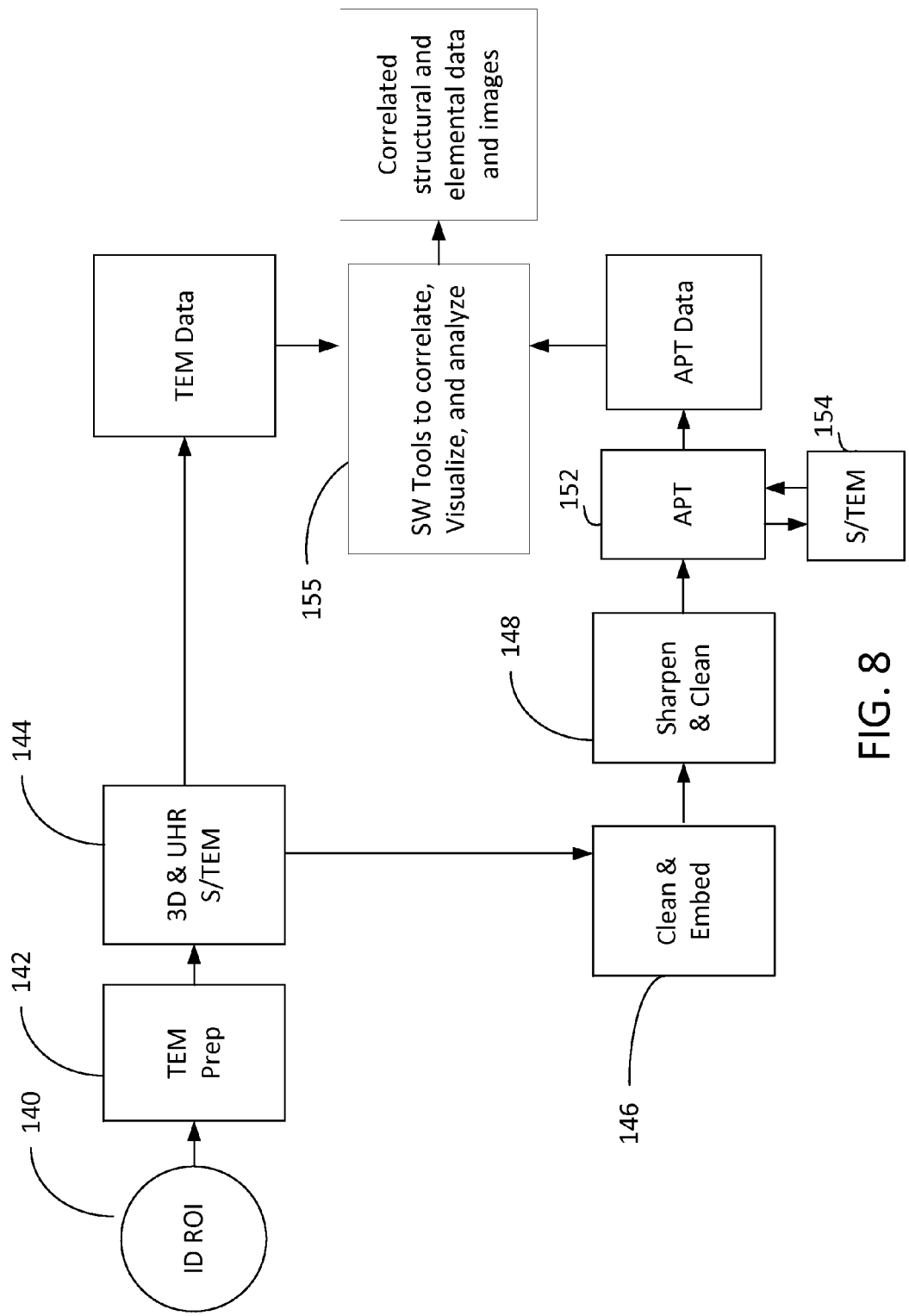
FIG. 8 is a flow chart showing the formation and analysis of a sample.
Figure 9:
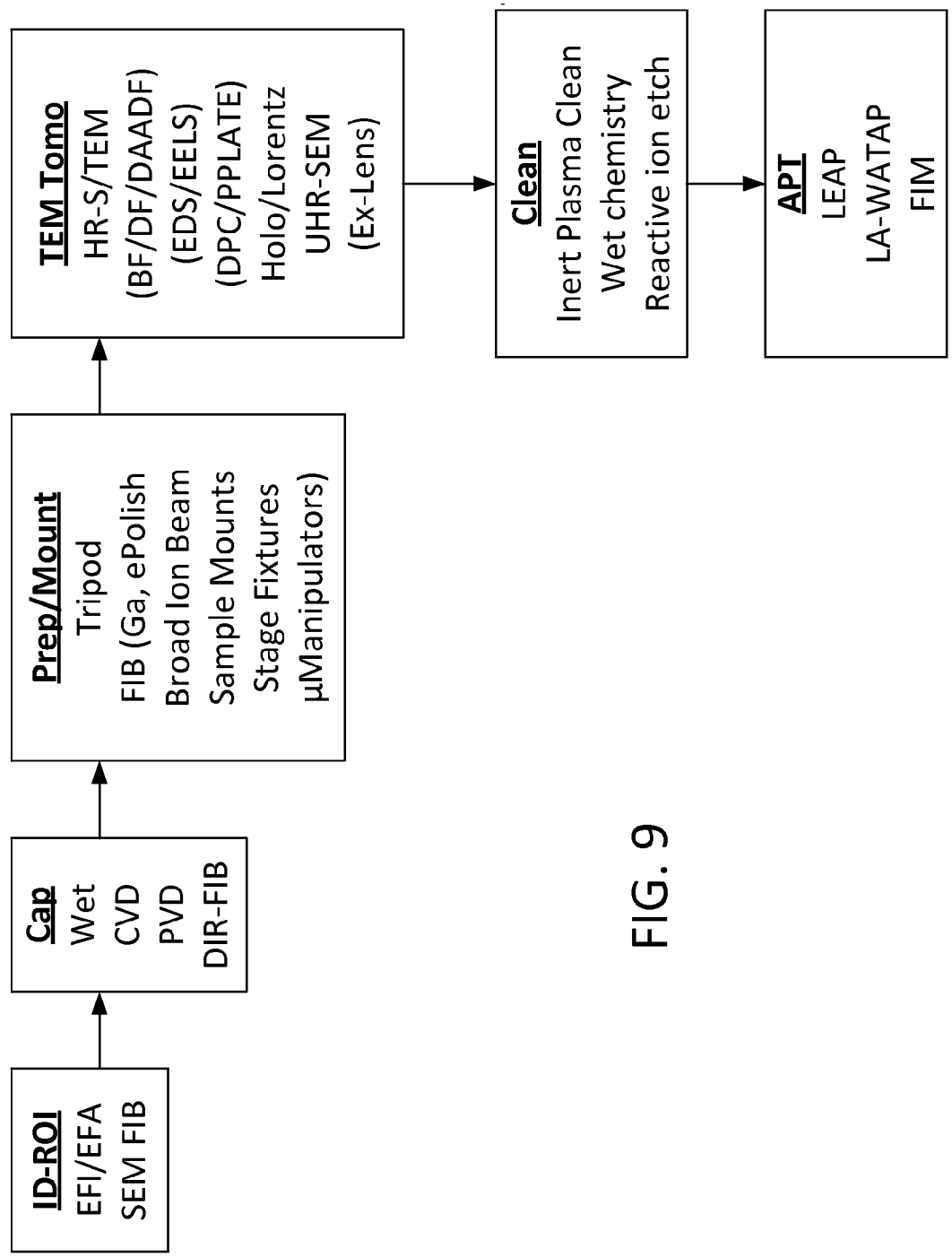
FIG. 9 is a generic flow chart for processing a sample for S/TEM and APM analysis.

FIG. 8 shows a flow chart of the process of forming the needle-shaped sample of this invention. To begin, the ROI is identified and isolated, or marked, as necessary in step 140. A lamella for the S/TEM is formed in step 142. The lamella sample is then studied with the S/TEM in step 144, which can include 3D and ultrahigh resolution (UHR) S/TEM. After the S/TEM study, the lamella sample is cleaned and coated or embedded within the coating apparatus in step 146. The sample is then subjected to the FIB milling process to form the needle-shaped sample in step 148. In step 150 the needle-shaped sample is studied with the APM in step 152 or iteratively studied in both APM and S/TEM 154 by moving the sample back and forth between the two instruments. The data obtained from the S/TEM and APM is then correlated using separate software tools in step 155 and the correlated structural and elemental data and images are displayed in step 157. FIG. 9 shows variations anticipated within each of the steps of the generic workflow shown in FIG. 8.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim as follows:

1. A method of analyzing a sample by both S/TEM and atom probe microscopy, comprising:
    forming a lamella having a region interest by processing a bulk material with a focused ion beam, wherein the lamella comprises a thickness of less than 200 nm;
    extracting the lamella from the bulk material using a micromanipulator;
    forming an image of the region of interest with an S/TEM (transmission electron microscope or scanning transmission electron microscope);
    depositing, using beam-induced deposition, physical vapor deposition, or chemical vapor deposition, a material onto the lamella after forming the image of the region of interest with the S/TEM to form a thicker structure with the lamella embedded, the material deposited onto the face of the lamella over the region of interest;
    forming a needle-shaped sample from the thicker structure with the lamella embedded by removing material from the thicker structure using ion beam milling; and
    forming an atom probe microscope image of the region of interest in the needle-shaped sample with an atomic probe microscope.

2. The method of claim 1 in which the step of forming the image of the region of interest with the atomic probe microscope includes forming multiple images of the needle shaped sample at different depths.

3. The method of claim 1 in which the step of forming the image of the region of interest with the S/TEM includes forming images of the sample at different angles relative to an electron beam of the S/TEM to form a three dimensional image of the region of interest by tomography.

4. The method of claim 1 further comprising combining on a display information derived from the S/TEM and information derived from the atom probe microscope.

5. The method of claim 1 in which the step of depositing the material onto the lamella is further characterized in that the material has a field evaporation property that compliments the elemental components within the region of interest.

6. The method of 1 further comprising positioning the lamella onto a mount compatible with both S/TEM and the atomic probe microscope, wherein the S/TEM comprises a scanning transmission electron microscope.

7. The method of claim 6, wherein the lamella has a top surface and is positioned on the mount in an orientation with the top surface substantially horizontal.

8. The method of claim 6, wherein the lamella has a top surface and is positioned on the mount in an orientation with the top surface substantially vertical.

9. The method of claim 6, wherein the lamella has a top surface and is positioned on the mount in an inverted orientation with the top surface connected to the mount.

10. The method of claim 1, wherein the step of depositing the material onto the lamella includes depositing a material having a mass that is different from the mass of the region of interest.

11. The method of claim 10, wherein the deposited material in the step of depositing the material onto the lamella comprises silicon, nickel, cobalt, and/or chrome.

12. The method of claim 1, wherein the region of interest is located between 30 nm and 2 micrometers from the tip of the needle shaped sample.

13. The method of claim 1, in which the step of depositing the material onto the lamella includes uniformly coating the lamella with a selected material.

14. The method of claim 1, in which the step of depositing the material onto the lamella includes depositing silicon by physical vapor deposition (PVD) or chemical vapor deposition (CVD).

15. The method of claim 1, in which the step of depositing material onto the lamella includes depositing nickel, cobalt, or chrome by PVD.

16. The method of claim 1 further comprising correlating S/TEM image data from the region of interest with atom probe microscope data from the region of interest.

17. The method of claim 16 in which correlating S/TEM image data from the region of interest with atom probe microscope data from the region of interest comprises reconstructing the three-dimensional microstructure and composition of the sample.

* * * * *